United States Patent
Mitragotri et al.

(10) Patent No.: US 6,620,123 B1
(45) Date of Patent: Sep. 16, 2003

(54) METHOD AND APPARATUS FOR PRODUCING HOMOGENOUS CAVITATION TO ENHANCE TRANSDERMAL TRANSPORT

(75) Inventors: Samir S. Mitragotri, Goleta, CA (US); Joseph Kost, Cambridge, MA (US); Scott C. Kellogg, Boston, MA (US); Nicholas F. Warner, Belmont, MA (US)

(73) Assignee: Sontra Medical, Inc., Cambridge, MA (US)

(*) Notice: Subject to any disclaimer, the term of this patent is extended or adjusted under 35 U.S.C. 154(b) by 0 days.

(21) Appl. No.: 09/868,443

(22) PCT Filed: Dec. 17, 1999

(86) PCT No.: PCT/US99/30067

§ 371 (c)(1), (2), (4) Date: Jul. 26, 2001

(87) PCT Pub. No.: WO00/35351

PCT Pub. Date: Jun. 22, 2000

(51) Int. Cl.⁷ .............................................. A61B 17/20
(52) U.S. Cl. ..................................................... 604/22
(58) Field of Search ........................... 604/22, 20, 890.1, 604/66, 289, 290; 601/2, 17; 607/154

(56) References Cited

U.S. PATENT DOCUMENTS

| | | | |
|---|---|---|---|
| 5,038,756 A | 8/1991 | Kepley | |
| 5,112,300 A | 5/1992 | Ureche | |
| 5,421,816 A | 6/1995 | Lipkovker | |
| 6,234,990 B1 * | 5/2001 | Rowe et al. | 604/22 |
| 6,392,327 B1 * | 5/2002 | Lewis et al. | 310/316.01 |

* cited by examiner

Primary Examiner—Manuel Mendez
(74) Attorney, Agent, or Firm—Hunton & Williams LLP

(57) ABSTRACT

The present invention is directed to apparatus and methods for producing homogenous cavitation. An ultrasound souce comprising an ultrasound transmitting element having an axis and a cross-section along the axis is disclosed The ultrasound transmitting element also has a first axial end and a second axial end operable to produce ultrasonic waves. The cross-section has an area having a maximum value at the first axial end and a minimum value at the second axial end. A method for producing homogenous cavitation at an area of skin comprises creating a volume of fluid having a uniformly dispersed concentration of cavitation nuclei adjacent the area of skin. Ultrasound is then applied to the volume of fluid and causes cavitation at the cavitation nuclei.

24 Claims, 4 Drawing Sheets

METHOD AND APPARATUS FOR PRODUCING HOMOGENOUS CAVITATION TO ENHANCE TRANSDERMAL TRANSPORT

FIELD OF THE INVENTION

This invention relates to transdermal molecular transportation. More specifically, this invention relates to methods and apparatus for producing homogenous cavitation in a transdermal transport system.

BACKGROUND OF THE INVENTION

Drugs are routinely administered either orally or by injection. The effectiveness of most drugs relies on achieving a certain concentration in the bloodstream. Although some drugs have inherent side effects which cannot be eliminated in any dosage form, many drugs exhibit undesirable behaviors that are specifically related to a particular route of administration. For example, drugs may be degraded in the GI tract by the low gastric pH, local enzymes or interaction with food or drink within the stomach. The drug or disease itself may forestall or compromise drug absorption because of vomiting or diarrhea. If a drug entity survives its trip through the GI tract, it may face rapid metabolism to pharmacologically inactive forms by the liver, the first-pass effect. Sometimes the drug itself has inherent undesirable attributes such as a short half-life, high potency or a narrow therapeutic blood level range.

Recently, efforts aimed at eliminating some of the problems of traditional dosage forms involve transdermal delivery of the drugs (TDD). Topical application has been used for a very long time, mostly in the treatment of localized skin diseases. Local treatment, however, only require that the drug permeate the outer layers of the skin to treat the diseased state, with little or no systemic accumulation. Transdermal delivery systems are designed for, inter alia, obtaining systemic blood levels, and topical drug application. For purposes of this application, the word "transdermal" is used as a generic term to describe the passage of substances to and through the skin.

TDD offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias in *Percutaneous Absorption: Mechanisms-Methodology-Drug Delivery*, Bronaugh, R. L. Maibach, H. I. (Ed), pp 1–12, Marcel Dekker, New York, 1989.

The transport of drugs through the skin is complex since many factors influence their permeation. These include the skin structure and its properties, the penetrating molecule and its physical-chemical relationship to the skin and the delivery matrix, and the combination of the skin, the penetrant, and the delivery system as a whole. Particularly, the skin is a complex structure. There are at least four distinct layers of tissue: the nonviable epidermis (stratum corneum, SC) the viable epidermis, the viable dermis, the subcutaneous connective tissue. Located within these layers are the skin's circulatory system, the arterial plexus, and appendages, including hair follicles, sebaceous glands, and sweat glands. The circulatory system lies in the dermis and tissues below the dermis. The capillaries do not actually enter the epidermal tissue but come within 150 to 200 microns of the outer surface of the skin.

In comparison to injections, TDD can reduce or eliminate the associated pain and the possibility of infection. Theoretically, the transdermal route of drug administration could be advantageous in the delivery of many therapeutic drugs, including proteins, because many drugs, including proteins, are susceptible to gastrointestinal degradation and exhibit poor gastrointestinal uptake, proteins such as interferon are cleared rapidly from the blood and need to be delivered at a sustained rate in order to maintain their blood concentration at a high value, and transdermal devices are easier to use than injections.

In spite of these advantages, very few drugs and no proteins or peptides are currently administered transdermally for clinical applications because of the low skin permeability to drugs. This low permeability is attributed to the SC, the outermost skin layer which consists of flat, dead cells filled with keratin fibers (keratinocytes) surrounded by lipid bilayers. The highly-ordered structure of the lipid bilayers confers an impermeable character to the SC (Flynn, G. L., in *Percutaneous Absorption: Mechanisms-Methodology-Drug Delivery.*; Bronaugh, R. L., Maibach, H. I. (Ed), pages 27–53, Marcel Dekker, New York 1989). Several methods have been proposed to enhance transdermal drug transport, including the use of chemical enhancers, i.e. the use of chemicals to either modify the skin structure or to increase the drug concentration in a transdermal patch (Burnette, R. R., in *Developmental Issues and Research Initiatives*; Hadgraft J., Guy, R. H., Eds., Marcel Dekker: 1989; pp. 247–288; Junginger, et al. in *Drug Permeation Enhancement*; Hsieh, D. S., Eds., pp. 59–90; Marcel Dekker, Inc. New York 1994) and the use of applications of electric fields to create transient transport pathways [electroporation] or to increase the mobility of charged drugs through the skin (iontophoresis) (Prausnitz *Proc. Natl. Acad. Sci. USA* 90, 10504–10508 (1993); Walters, K. A., in *Transdermal Drug Delivery: Developmental Issues and Research Initiatives*, Ed. Hadgraft J., Guy, R. H., Marcel Dekker, 1989). Another approach that has been explored is the application of ultrasound.

Ultrasound has been shown to enhance transdermal transport of low-molecular weight drugs (molecular weight less than 500) across human skin, a phenomenon referred to as sonophoresis (Levy, J. Clin. Invest. 1989, 83, 2974–2078; Kost and Langer in "*Topical Drug Bioavailability, Bioequivalence, and Penetration*"; pp. 91–103, Shah V. P., Maibach H. I., Eds. (Plenum: New York, 1993); Frideman, R. M., "*Interferons: A Primer*", Academic Press, New York, 1981). For example, U.S. Pat. No. 4,309,989 to Fahim and U.S. Pat. No. 4,767,402 issued to Kost et al. both describe the use of ultrasound in conjunction with transdermal drug delivery. U.S. Pat. No. 4,309,989 discloses the topical application of a medication using ultrasound with a coupling agent such as oil. Ultrasound at a frequency of at least 1000 kHz and a power of one to three W/cm$^2$ was used to cause selective localized intracellular concentration of a zinc containing compound for the treatment of herpes simplex virus.

U.S. Pat. No. 4,309,989, the disclosure of which is specifically incorporated by reference, discloses the use of ultrasound for enhancing and controlling transdermal permeation of a molecule, including drugs, antigens, vitamins, inorganic and organic compounds, and various combinations of these substances, through the skin and into the circulatory system. Ultrasound having a frequency between about 20 kHz. and 10 MHz. and having an intensity between about 0 and 3 W/cm$^2$ is used essentially to drive molecules through the skin and into the circulatory system. A significant drawback to this system is that the resultant enhanced permeability only occurs while the ultrasound is being applied to the skin. Thus, the skin is often damaged due to over exposure to the ultrasound.

Although a variety of ultrasound conditions have been used for sonophoresis, the most commonly used conditions correspond to therapeutic ultrasound (frequency in the range of between one MHz and three MHz, and intensity in the range of between above zero and two W/cm$^2$) (such as that described in the Kost et al. patent). It is a common observation that the typical enhancement induced by therapeutic ultrasound is less than ten-fold. In many cases, no enhancement of transdermal drug transport has been observed upon ultrasound application. Accordingly, a better selection of ultrasound techniques is needed to induce a higher enhancement of transdermal drug transport by sonophoresis.

Application of low-frequency (between approximately 20 and 200 kHz) ultrasound can dramatically enhance transdermal transport of drugs, as described in PCT/US96/12244 by Massachusetts Institute of Technology. Transdermal transport enhancement induced by low-frequency ultrasound was found to be as much as 1000-fold higher than that induced by therapeutic ultrasound. Another advantage of low-frequency sonophoresis as compared to therapeutic ultrasound is that the former can induce transdermal transport of drugs which do not passively permeate across the skin.

In addition to there being a need to deliver drugs through the skin, there is a major medical need to extract analytes through the skin. For example, it is desirable for diabetics to measure blood glucose several times per day in order to optimize insulin treatment and thereby reduce the severe long-term complications of the disease. Currently, diabetics do this by pricking the highly vascularized fingertips with a lancet to perforate the skin, then milking the skin with manual pressure to produce a drop of blood, which is then assayed for glucose using a disposable diagnostic strip and a meter into which this strip fits. This method of glucose measurement has the major disadvantage that it is painful, so diabetics do not like to obtain a glucose measurement as often as is medically indicated.

Therefore, many groups are working on non-invasive and less invasive means to measure glucose, such as micro lancets that are very small in diameter, very sharp, and penetrate only to the interstitium (not to the blood vessels of the dermis). A small sample, from about 0.1 to two $\mu$l, of interstitial fluid is obtained through capillary forces for glucose measurements. Other groups have used a laser to breach the integrity of the stratum corneum and thereby make it possible for blood or interstitial fluid to diffuse out of such a hole or to be obtained through such a hole using pneumatic force (suction) or other techniques. An example of such a laser based sampling device is disclosed in U.S. Pat. No. 5,165,418 to Tankovich and WPI ACC No: 94-167045/20 by Budnik (assigned to Venisect, Inc.).

A problem with methods that penetrate the skin to obtain interstitial fluid is that interstitial fluid occurs in the body in a gel like form with little free fluid and in fact is even negative pressure that limits the amount of free interstitial fluid that can be obtained. When a very small hole is made in the skin, penetrating to a depth such that interstitial fluid is available, it takes a great deal of mechanical force (milking, vacuum, or other force) to obtain the quantity of blood used in a glucose meter.

Thus, there has been described methods for application of ultrasound and extraction of analyte that rely on techniques known in the art such as are disclosed in U.S. patent application Ser. No. 08/885,931 filed Jun. 30, 1997, the disclosure of which is hereby incorporated by reference. The methods described therein channel or focus an ultrasound beam onto a small area of skin. In some embodiments, methods and devices utilizing a chamber and ultrasound probe disclosed can be used to non-invasively extract analyte and deliver drugs (i.e., broadly transdermally transport substances). This provides many advantages, including the ability to create a small puncture or localized erosion of the skin tissue, without a large degree of concomitant pain. The number of pain receptors within the ultrasound application site decreases as the application area decreases. Thus, the application of ultrasound to a very small area will produce less sensation and allow ultrasound and/or its local effects to be administered at higher intensities with little pain or discomfort. Channeling of ultrasound geometrically is one way to apply ultrasound to a small area. The oscillation of a small element near or in contact with the surface of the skin is another way to apply ultrasound to a small area. Large forces can be produced locally, resulting in cavitation, mechanical oscillations in the skin itself, and large localized shearing forces near the surface of the skin. The element can also produce acoustic streaming, which refers to the large convective flows produced by ultrasound. This appears to aid in obtaining a sample of blood or interstitial fluid without having to "milk" the puncture site. Ultrasound transducers are known to rapidly heat under continuous operation, reaching temperatures that can cause skin damage. Heat damage to the skin can be minimized by using a transducer that is located away from the skin to oscillate a small element near the skin. In the case of analyte extraction, compounds present on the surface of and/or in the skin can contaminate the extracted sample. The level of contamination increases as skin surface area increases. Surface contamination can be minimized by minimizing the surface area of ultrasound application. Thus, skin permeability can be increased locally, and transiently through the use of the methods and devices described herein, for either drug delivery or measurement of analyte.

Moreover, it has been disclosed that the application of ultrasound is only required once for multiple deliveries or extractions over an extended period of time rather than prior to each extraction or delivery. That is, it has been shown that if ultrasound having a particular frequency and a particular intensity of is applied, multiple analyte extractions or drug deliveries may be performed over an extended period of time. For example, if ultrasound having a frequency of 20 kHz. and an intensity of 10 W/cm$^2$ is applied, the skin retains an increased permeability for a period of up to four hours. This is described more particularly in U.S. Provisional Patent Application No. 60/070,813 filed on Jan. 8, 1998, the disclosure of which is specifically incorporated by reference herein.

Nevertheless, the amount (e.g., duration, intensity, duty cycle etc.) of ultrasound necessary to achieve this permeability enhancement varies widely. Several factors on the nature of skin must be considered. For example, the type of skin which the substance is to pass through varies from species to species, varies according to age, with the skin of an infant having a greater permeability than that of an older adult, varies according to local composition, thickness and density, varies as a function of injury or exposure to agents such as organic solvents or surfactants, and varies as a function of some diseases such as psoriasis or abrasion.

When cavitation is relied upon to enhance transdermal transport, care must be taken to avoid excessive cavitation which can do damage to the skin through the localized increases of heat and pressure characteristic with cavitation phenomena. If the cavitation produced is sporadic or nonuniform, it very difficult to prevent the localized heat and pressure increases.

SUMMARY OF THE INVENTION

Therefore, a need has arisen for a method and apparatus that provides homogenous cavitation for use in a transdermal transport system.

According to one embodiment, the present invention comprises an improved ultrasound source. The ultrasound source comprises an ultrasound transmitting element having an axis and a first cross-section along said axis. The ultrasound transmitting element also has a first axial end operable to produce ultrasonic waves and a second axial end. The first axial end comprises a matrix of ultrasound producing portions.

According to another embodiment, the present invention comprises an ultrasound source. The ultrasound souce comprises an ultrasound transmitting element having an axis and a cross-section along the axis. The ultrasound transmitting element also has a first axial end and a second axial end operable to produce ultrasonic waves. The cross-section has an area having a maximum value at the first axial end and a minimum value at the second axial end.

According to another embodiment, the present invention comprises a method for producing homogenous cavitation at an area of skin. The method comprises creating a volume of fluid having a uniformly dispersed concentration of cavitation nuclei adjacent the area of skin. Ultrasound is then applied to the volume of fluid and causes cavitation at the cavitation nuclei.

According to another embodiment, the present invention comprises a method for producing homogenous cavitation at an area of skin. The method comprises creating a volume of fluid having a uniformly dispersed concentration of a first substance adjacent the area of skin. The first substance is a substance that facilitates the production of cavitation. Ultrasound is then applied to the volume of fluid to cause cavitation.

According to another embodiment, the present invention comprises a method for producing homogenous cavitation at an area of skin. An ultrasound source is provided to apply an ultrasonic wave to the area of skin. A screen having a number of opening therein is positioned between the area of skin and the ultrasound source. Finally, ultrasound is applied to the area of skin through the screen. The openings in the screen nucleate cavitation and control the size of cavitation bubbles produced.

According to another embodiment, the present invention comprises an ultrasound device. The ultrasound device includes an ultrasound horn and a housing for the ultrasound horn. The housing has a portion with a reduced inside diameter relative to a diameter of the horn. The reduced inside diameter focuses ultrasonic energy on a small area of skin.

BRIEF DESCRIPTION OF THE DRAWINGS

The features and objects of the present invention, and the manner of attaining them is explained in detail in the following DETAILED DESCRIPTION OF THE PREFERRED EMBODIMENTS of the invention when taken in conjunction with the accompanying drawings wherein.

DETAILED DESCRIPTION OF THE PREFERRED EMBODIMENTS

The use of ultrasound to facilitate transdermal transport is known. The mechanism by which ultrasound is used to facilitate transdermal transport has differed. In the context of transdermal delivery systems, ultrasound was initially used as a driving force that essentially pushed drugs through the skin and into the circulatory system. Ultrasound is also used to increase the permeability of the skin. That is, application of ultrasound having a particular frequency will disorganize the lipid bilayer in the skin and thus increase the permeability of the skin. In this context, either drugs can be delivered through the skin to the body or analyte can be extracted through the skin from the body. A driving force of some type is still required, but the required intensity of the driving force is decreased. For example, a concentration gradient is generally sufficient driving force for transdermal transport through skin whose permeability has been enhanced using ultrasound.

The permeability enhancement that results from the application of ultrasound is due, at least in part, to cavitation that is caused by the ultrasound. When used to irradiate a liquid medium such as the coupling medium used in conjunction with the present invention, certain ultrasonic fields will cause cavitation in the liquid. Broadly defined, cavitation is the formation of vapor- or gas-filled cavities in liquids when subjected to mechanical forces. One problem with being able to effectively use cavitation to enhance skin permeability is that cavitation is not readily predictable or controllable. In the context of a transdermal delivery system, cavitation that is inconsistent and unevenly dispersed is not as effective at enhancing skin permeability as cavitation that is consistent and evenly dispersed. Moreover, cavitation that is highly localized may cause skin damage. This application describes various apparatus and methods the inventors have found to produce consistent, evenly dispersed cavitation.

Ultrasound is created and transmitted using a combination of a transducer and horn. The transducer, converts an electrical impulse into a mechanical vibration and the horn transmits that mechanical vibration to a medium. The configuration of the horn determines the wave pattern of the ultrasound being transmitted to the medium. Moreover, the wave pattern of the ultrasound is, at least in part, responsible for the cavitation. Therefore, the horn configuration directly affects the amount and dispersement of the cavitation caused by an ultrasonic wave. The inventors have found a number of horn configurations that produce a wave pattern that causes evenly dispersed and consistent cavitation.

Figure 1A:
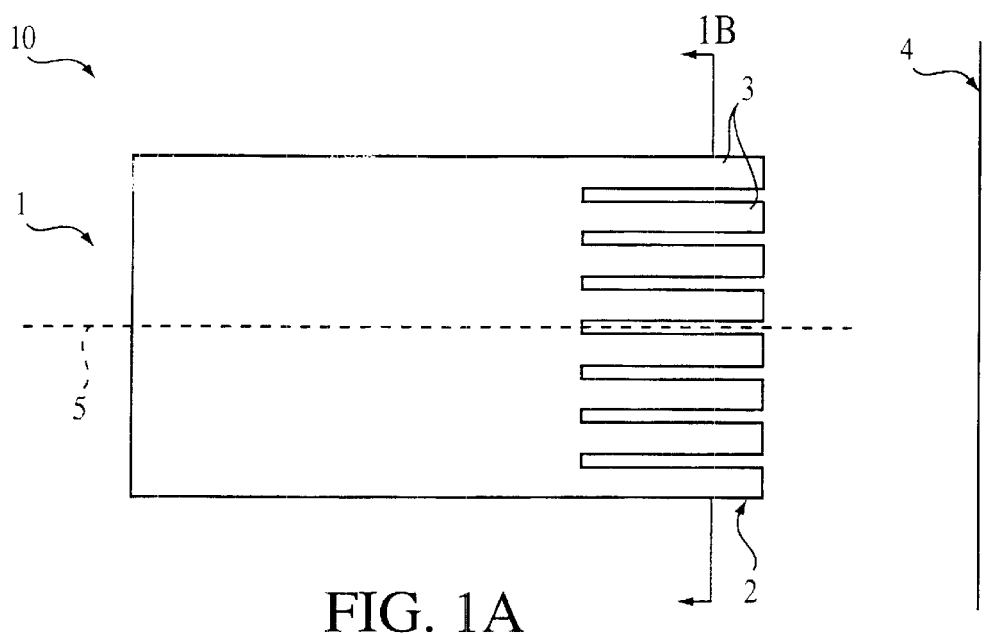
FIGS. 1a and 1b depict an ultrasonic horn configuration according to one embodiment of the present invention.
Figure 1B:
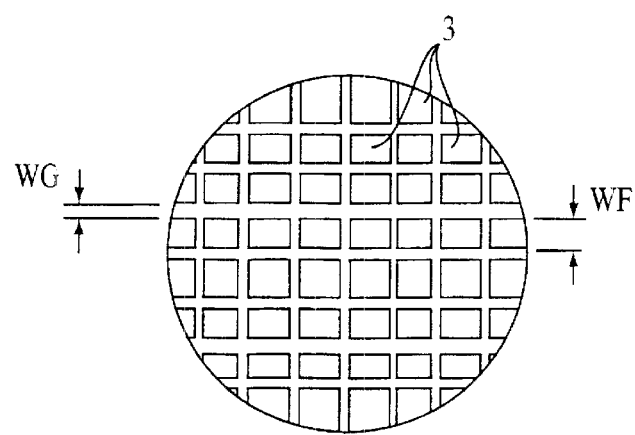

According to one embodiment, the present invention comprises an ultrasonic horn configuration including a number of ultrasound producing portions or "fingers" that produce evenly dispersed cavitation. As shown in FIG. 1, cylindrical shaped ultrasound horn 10 having an axis 5 comprises a first axial end 1, a second axial end 2 and a plurality of ultrasound producing portions 3. Ultrasound horn 10 is generally connected to a transducer at its first axial end 1. The transducer transmits a vibration to horn 10 and the vibration is, in turn, transmitted to a fluid medium at second axial end 2 of horn 10.

Second axial end 2 of horn 10 is configured to include a plurality of ultrasound producing portions or fingers 3. Each ultrasound producing portion 3 produces a separate ultrasonic wave and therefore a separate cavitation source. Moreover, in operation the ultrasonic wave produced by each finger 3 is in phase with and overlaps with the ultrasonic waves produced by its neighboring fingers. This overlap results in more evenly distributed ultrasound that in turn leads to more evenly distributed cavitation.

In the environment of an apparatus used to enhance the permeability of the skin, ultrasound horn 10 is preferably configured so that the more evenly distributed cavitation occurs at or near the surface of the skin. This is accomplished by controlling the width of each finger, WF, the width of the gaps between the fingers, WG, and the distance, D, between the second axial end of the horn and the skin surface 4.

Ultrasound producing portions 3 can be fabricated on the end of horn 10 in a number of ways depending on the material used for horn 10. For example, if horn 10 is made of metal, fingers 3 may be configured on the second axial end of horn 10 by making a number of cuts through horn 10 in parallel with axis 5. These cuts can be made, for example, by and electrical discharge manufacturing process. This can be used to produce a matrix of ultrasound producing portions such as is shown in FIG. 1. In other embodiments, ultrasound producing portions 3 are affixed to second axial end 2 of horn 10 by for example by press fitting the fingers into the end of horn 10. The fingers are preferably made from a hard and durable material such as titanium, and carbide steel. Other materials such as, stainless steel, aluminum, ceramic and glass could be used.

Horn 10 is shown as a cylindrical horn having ultrasound producing portions having a square cross-section along the horn axis. But, the horn and ultrasound producing portions could have many different shapes and many different combinations of shapes. For example, the horn could be a bar shaped horn having a square cross-section and the fingers could be cylindrical with a circular cross-section. Further, the number of fingers configured on the end of the horn can vary. The number of fingers will determine the necessary dimensions WG and WF.

According to another embodiment, the present invention comprises an ultrasonic horn having a "bullet" configuration that produces a cavitation effect that spreads out over the surface of the skin 24. As shown in FIGS. 2, bullet shaped ultrasound horn 20 having an axis 25 comprises a first axial end 21, a second axial end 22 having a tapered or bullet shaped configuration. Ultrasound horn 20 is generally connected to a transducer at its first axial end 21. The transducer transmits a vibration to horn 20 and the vibration is, in turn, transmitted to a fluid medium at second axial end 22 of horn 20.

Figure 2A:
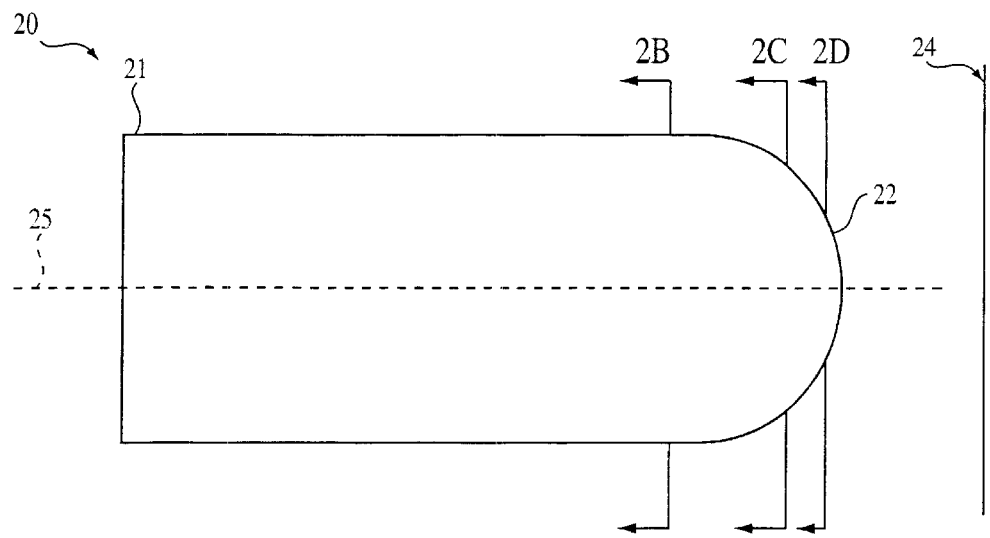
FIGS. 2a–2d depict an ultrasonic horn configuration according to another embodiment of the present invention.
Figure 2B:
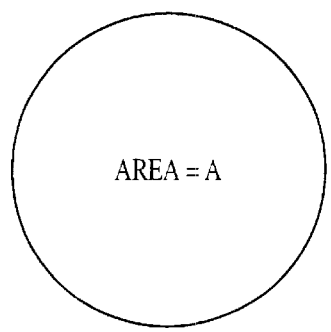
Figure 2C:
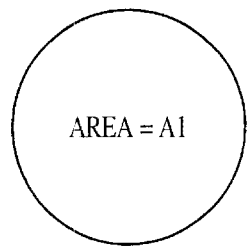
Figure 2D:
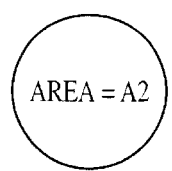

Second axial end 22 of horn 20 is configured to include a bullet shape. That is, the cross-section along axis 25 of horn 20 varies in size between first axial end 21 and second axial end 22. More specifically, the axial cross-section has an area having a maximum value at first axial end 21 and a minimum value at second axial end 22. Referring particularly to FIGS. 2b, 2c and 2d, various cross sections of horn 20 are shown. As is readily apparent, the area A is greater than the area A1, and the area A1 is greater than the area A2; A2 being the area of the cross-section nearest the second axial end of horn 20 and A being the area of the cross-section nearest the first axial end of horn 20. In operation, the ultrasonic wave produced by this bullet shaped configuration gradually spreads out as the distance from second axial end 22 increases and leads to cavitation that spreads out over skin surface 24.

This extent of the spreading out effect can be optimized somewhat by controlling the rate of decrease of the cross-sectional area of horn 20. In general, as the rate of area reduction increases, that is, horn 20 becomes more tapered, the spreading effect becomes greater up to the point where second axial end 22 has a spherical configuration.

Horn 20 can be fabricated from any suitable material. The bullet configuration can be formed at second axial end of horn 20 using any suitable machining process. For example, second axial end 22 can be turned on a lathe to the bullet configuration.

Horn 20 is shown as a cylindrical horn. Nevertheless, a similar spreading effect can be obtained by machining the bullet configuration at the second axial end of any horn. For example, a bar shaped horn having a square cross-section along the horn axis could be configured with a bullet shaped end.

Figure 3A:
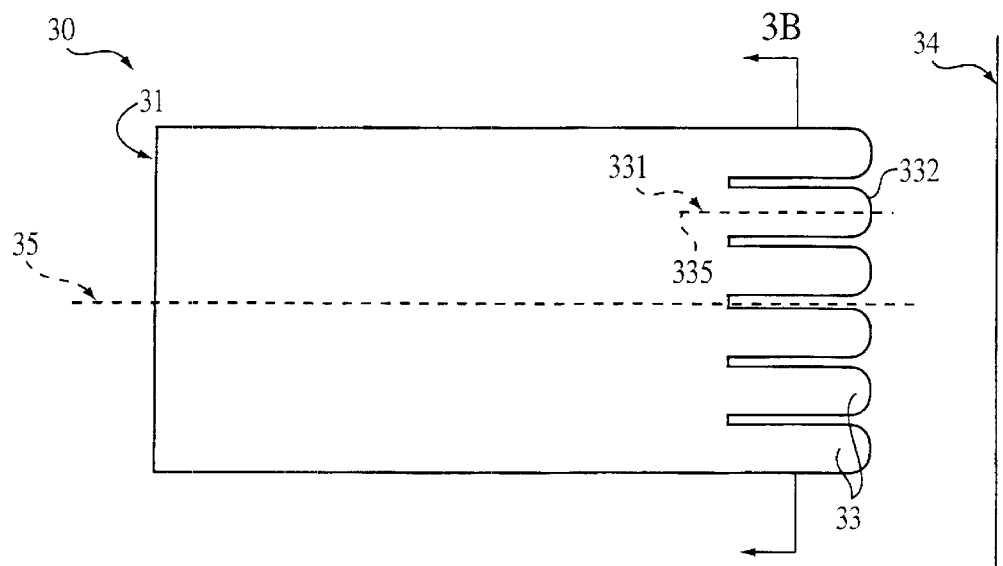
FIGS. 3a and 3b depict an ultrasonic horn configuration according to another embodiment of the present invention.
Figure 3B:
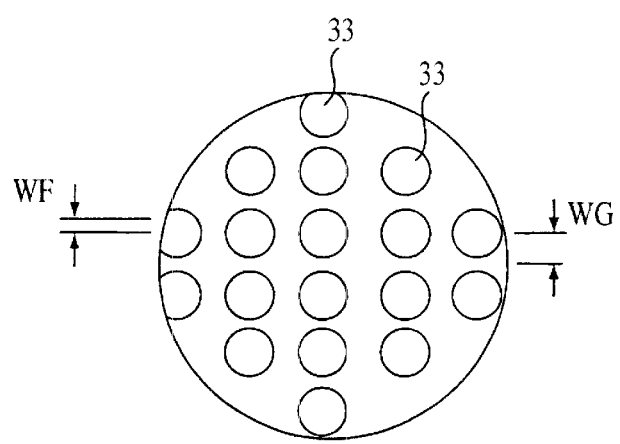

According to another embodiment, the present invention comprises an ultrasonic horn that combines the beneficial features of the finger horn and bullet horn described in conjunction with FIGS. 1 and 2. As shown in FIGS. 3, ultrasound horn 30 having an axis 35 comprises a first axial end 31, a second axial end 32, and a plurality of ultrasound producing portions 33. Ultrasound horn 30 is generally connected to a transducer at its first axial end 31. The transducer transmits a vibration to horn 30 and the vibration is, in turn, transmitted to a fluid medium at second axial end 32 of horn 30.

Second axial end 32 of horn 30 is configured to include a plurality of ultrasound producing portions or fingers 33. Each ultrasound producing portion 33 has a tapered or bullet shaped configuration and generates a separate ultrasonic wave that produces a cavitation effect that spreads out over the surface of the skin 34. In operation the ultrasonic wave produced by each finger 33 is in phase with and overlaps with the ultrasonic waves produced by its neighboring fingers. This overlap results in more evenly distributed ultrasound that in turn leads to more evenly distributed cavitation.

Each bullet shaped finger 33 has an axis 335 and a cross-section that varies in size between a first axial end 331 and a second axial end 332. More specifically, the axial cross-section has an area having a maximum value at first axial end 331 and a minimum value at second axial end 332. Horn 30 is depicted as having eighteen fingers only for ease of illustration. In a preferred embodiment, horn 30 has a number of figures necessary to produce a desired cavitation pattern. According to one embodiment, horn 30 is configured to have about 60 fingers.

In the environment of an apparatus used to enhance the permeability of the skin, ultrasound horn 30 is preferably configured so that the more evenly distributed cavitation occurs at or near the surface of the skin. This is accomplished by controlling the width of each finger, WF, the width of the gaps between the fingers, WG, and the distance, D, between the second axial end of the horn and the skin surface 34.

Horn 30 is shown as a cylindrical horn. Nevertheless, horn 30 may have many different configurations. For example, bullet shaped fingers could be a incorporated into a bar shaped horn having a square cross-section. Further, the number of fingers configured on the end of horn 30 can vary. The number of fingers will determine the necessary dimensions WG and WF.

Ultrasound transducers endure a great stress in normal operation. For example, cavitation can cause localized hot spots and high pressure gradients. Extended exposure to ultrasound and cavitation can cause pitting of the ultrasound. Pitting of an ultrasound horn quickly leads to accelerated decay, because the nonuniformities in the horn act as cavitation nuclei and therefore lead to cavitation occurring at the surface of the horn. Moreover, when cavitation occurs at the surface of the horn, it interrupts further transmission of the ultrasonic wave and therefore diminishes the amount of cavitation occurring elsewhere. In the context of an apparatus for enhancing skin permeability, this is disadvantageous because it reduces the effectiveness of the ultrasound. Exposure times need to be increased to enhance permeability, thus increasing the chance of over exposure to ultrasound.

Therefore, according to another embodiment, the present invention comprises a highly durable ultrasound horn. According to one embodiment the present invention comprises an ultrasound horn comprised of a carbide steel tip. In another embodiment, the present invention comprises an ultrasound horn that has an anodized hard coating. The use of carbide steel is generally limited to the tip of the horn to minimize losses. An anodized coating can be used on the entire horn or simply the ultrasound radiating portion. The teachings of this embodiment of the present invention could be applied to any configuration of ultrasound horn including any of the horns shown and described in FIGS. 1–4. For example, in the context of FIG. 1, an improved ultrasound horn 10 is formed by fabricating ultrasound radiating portions 3 from carbide steel. According to another example, an improved ultrasound horn 10 is formed by anodizing the entire horn to after fabrication. Both the use of an anodized coating or carbide steel provide an ultrasound horn having enhanced durability and resistance to pitting.

Similarly, according to another embodiment, the present invention comprises a highly polished ultrasound horn. For reasons discussed above, a highly polished ultrasound horn produces more consistent and homogenous cavitation. By polishing the ultrasound horn, nonuniformities are removed from the surface of the horn. This, in turn, limits the chance of sporadic cavitation at the horn surface.

According to another embodiment, the present invention comprises a method of producing consistent and evenly dispersed cavitation using a cavitation screen. Structurally, the cavitation screen is a screen as that term is conventionally used. That is, a cavitation screen according to embodiments of the present invention is a flat, planar object having a matrix of openings therein. The cavitation screen is preferably formed from a durable and non-corrosive material such as metal. The cavitation screen may also be treated or coated with durable coating so that it is more resistant to the effects of ultrasound. For example, the screen may be anodized.

Operationally, the cavitation screen is positioned between an ultrasound horn and the object to which ultrasound is to be applied. The cavitation screen enables transmission and growth of consistent bubbles. The openings in the screen nucleate cavitation and filter the bubbles produced by cavitation. That is, cavitation bubbles may still be produced throughout the liquid, but the screen acts to break the bubbles that are larger than the size of the openings in the screen. The size of the openings can be adjusted to produce the cavitation desired. Further, in the context of an apparatus for enhancing skin permeability, the screen may be positioned anywhere between the horn and the skin. If the screen is positioned close to the horn, the cavitation will be somewhat separated from the skin surface and have a lesser effect. If the screen is moved closer to the skin, the cavitation also occurs closer to the skin and therefore will have a more pronounced effect on skin permeability.

According to another embodiment, the present invention comprises a method of producing consistent and evenly dispersed cavitation by "seeding" the coupling medium with cavitation nuclei. More, specifically, it has been found that the addition of particles to the coupling medium used in an apparatus for enhancing skin permeability leads to more consistent cavitation. Each particle dispersed within the coupling medium acts as a cavitation nuclei. Therefore, if particles are evenly dispersed throughout the coupling medium, more consistent and evenly dispersed cavitation results. The particles may be formed from ceramics, polystyrene, titanium dioxide or any other metal or polymer. The particles are sized appropriately for dispersion in the coupling medium. In one embodiment, the particles are 1–20 $\mu$m in diameter. Smaller or larger sizes are possible. The concentration of particles used should be appropriate for dispersion in the coupling medium. In one embodiment 5–10 mg/ml of particles are used. The concentration of particles used varies depending on the type of particles used and the coupling medium.

In a related embodiment, dissolved gas, such as $O_2$ is used in the coupling medium to "seed" cavitation. If the dissolved gas is in the form of bubbles, these bubbles act as cavitation nuclei. If the dissolved gas exists at the molecular level, it diffuses into cavitation bubbles and enhances growth. The cavitation enhancement is directly proportional to the amount of dissolved gas in the medium. Therefore, by controlling the dissolved gas concentration in the medium, the amount of cavitation produced by ultrasound can be controlled. Any suitable gas may be used to enhance cavitation. Suitable gasses include, for example, oxygen, zenon, neon, argon, krypton and helium. If oxygen is used as the gas, a concentration of about 5 mg/dl is provided in the coupling medium. Other concentrations are possible and within the scope of the present invention.

In another embodiment, the present invention comprises a method for producing consistent and evenly dispersed cavitation by dissolving chemicals in the coupling medium. Certain chemicals have properties that are helpful for producing consistent cavitation. In one embodiment, fluorocarbons are added to the coupling medium in an attempt to produce more consistent cavitation. Fluorocarbons have a very low boiling point. Therefore, when fluorocarbons are subjected to ultrasound they tend to evaporate. This evaporation causes gas bubbles in the coupling medium. These gas bubbles, in turn, act as cavitation nuclei and thus produce consistent cavitation. The amount of fluorocarbon added to the coupling medium can be adjusted based on the desired amount of cavitation. Suitable fluorocarbons include, for example, perfluoropentane, perfluorohexane and similar molecules. In one embodiment, the fluorocarbons are used at a concentration of 5–10 mg/ml. Other concentrations are possible and within the scope of the present invention.

Similarly, surfactants can be added to the coupling medium to produce more consistent cavitation by a different mechanism. The use of surfactants in the coupling medium does not "seed" cavitation as the above methods do. Rather, by adding surfactant to the coupling medium, the surface tension of the coupling medium is reduced. This reduced surface tension makes it easier for cavitation to occur by making it easier for bubbles to form in the medium. Suitable surfactants include sodium lauryl sulfate and fatty alcohols, for example, dodecanol.

In another embodiment, the present invention comprises a method for producing consistent and evenly dispersed cavitation by pretreating the skin with chemicals or cavitation nuclei. In one embodiment, the skin surface to be subjected to ultrasound is wiped with a chemical cleansing agent that removes inhomogeneities from the skin surface.

The removal of inhomogeneities from the skin surface leads to more consistent cavitation by removing substances that could act as cavitation nuclei and cause sporadic, localized cavitation that could damage the skin. Alhocols such as ethanol and isopropyl alcohol are suitable for use to pretreat the skin.

In another embodiment, the skin to be treated with ultrasound is presoaked with cavitation nuclei to produce more consistent cavitation. The cavitation nuclei could be in any of the forms discussed above. According to one embodiment, the skin is presoaked with solution having evenly dispersed and very fine particles. The particles evenly distribute themselves on the surface of the skin. This results in consistent and evenly dispersed cavitation when ultrasound is applied. In another embodiment, the skin is presoaked with a liquid having a high dissolved gas content. Similar to above, when ultrasound is applied, the dissolved gas acts as cavitation nuclei and thus produces consistent cavitation.

Figure 4:
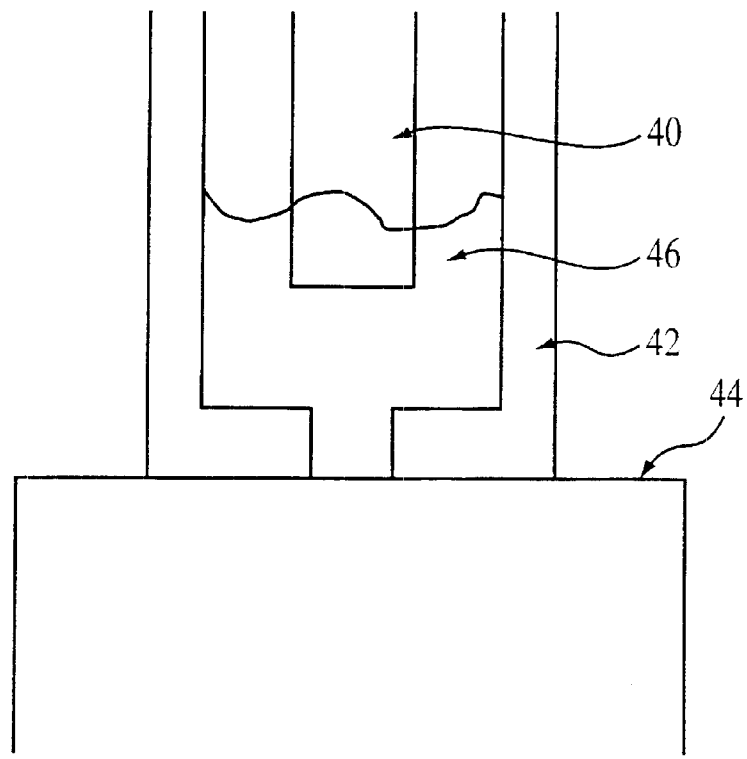
FIG. 4 depicts an ultrasound configuration according to another embodiment of the present invention.

Referring to FIG. 4, an ultrasound configuration according to another embodiment of the present invention is provided. Ultrasonic horn 40 may be used in conjunction with transducer housing 42 that has a reduced inside diameter, relative to horn 40, where housing 42 is in contact with skin 44. Ultrasonic horn may be coupled with skin 44 through coupling medium 46. The walls of reduced diameter housing 42 mask a significant portion of skin 44, and expose only a fraction of skin 44 to ultrasound.

The cavitation effect on the skin is generally most pronounced in the center. Therefore, through this configuration, the level of permeability enhancement achieved is centralized of the treated skin.

Other methods, such as a pin horn and accoustic channeling, may be used to produce a similar effect on the skin.

The above embodiments focus on methods and apparatus used to produce consistent and homogenous cavitation. As will be apparent to one of ordinary skill in the art, these methods are not mutually exclusive. The methods and apparatus can be combined to provide even greater control of cavitation. For example, any of the horns shown in FIGS. 1–4 can be used in conjunction with the addition of cavitation nuclei to the coupling medium. Similarly, both chemicals and cavitation nuclei could be added to the coupling medium for an enhanced effect. The area of skin can be pretreated in conjunction with any of the above apparatus and methods.

Although the present invention has been described in detail, it should be understood that various changes, substitutions, and alterations can be made without departing from the intended scope as defined by the appended claims.

What is claimed is:

1. An ultrasound source comprising:
    an ultrasound transmitting element having an axis and a first cross-section along said axis, said ultrasound transmitting element having a first axial end and a second axial end, said first axial end operable to produce ultrasonic waves; and
    said first axial end comprising a matrix of ultrasound producing portions, said portions defined by a first series of parallel axial cuts and a second series of parallel axial cuts, said second series of parallel axial cuts are approximately perpendicular to said first series of parallel axial cuts and said matrix having the first cross-section;
    wherein the ultrasound producing portions, which are completely bounded by said cuts, each has a substantially rectangular cross-section parallel to said first cross-section.

2. The ultrasound source of claim 1 wherein said ultrasound transmitting element comprises a cylindrical horn and said first cross-section is a circle.

3. The ultrasound source of claim 1 wherein said ultrasound transmitting element comprises a flat horn and said first cross-section is rectangular.

4. The ultrasound source of claim 3 wherein said matrix of ultrasound producing portions comprises a row of ultrasound producing portions.

5. The ultrasound source of claim 1 wherein each one of said ultrasound producing portions has a first end proximal to the ultrasound transmitting element and a second end distal to the ultrasound transmitting element.

6. The ultrasound source of claim 1 wherein the first axial end radiates ultrasound toward a skin surface and causes cavitation in a coupling medium, at the skin surface or in the skin.

7. The ultrasound source of claim 1 wherein said first end comprises an anodized coating.

8. The ultrasound source of claim 1 wherein said first end comprises carbide steel.

9. The ultrasound source of claim 8 wherein said carbide steel first end is bonded to said ultrasound transmitting element.

10. An ultrasound source comprising:
    an ultrasound transmitting element having an axis and a cross-section along said axis, said ultrasound transmitting element having a first axial end and a second axial end, said second axial end operable to produce ultrasonic waves;
    said cross-section having an area having a maximum value at the first axial end and a minimum value at the second axial end; and
    said first axial end comprising a matrix of ultrasound producing portions, said portions defined by a first series of parallel axial cuts and a second series of parallel axial cuts, said second series of parallel axial cuts are approximately perpendicular to said first series of parallel axial cuts and said matrix having the first cross-section;
    wherein the ultrasound producing portions, which are completely bounded by said cuts, each has a substantially rectangular cross-section parallel to said first cross-section.

11. The ultrasound source of claim 10 wherein said cross-section has a uniform shape.

12. The ultrasound source of claim 10 wherein said ultrasound transmitting element has a circular cross-section along said axis.

13. The ultrasound source of claim 10 wherein the ultrasound transmitting element produces an ultrasound wave pattern that produces uniformly distributed cavitation.

14. The ultrasound source of claim 10 wherein the first axial end radiates ultrasound toward a skin surface and causes uniformly distributed cavitation in a coupling medium, at the skin surface or in the skin.

15. The ultrasound source of claim 10 wherein said first end comprises an anodized coating.

16. The ultrasound source of claim 10 wherein said first end comprises carbide steel.

17. The ultrasound source of claim 16 wherein said carbide steel first end is bonded to said ultrasound transmitting element.

18. A method for producing homogenous cavitation at an area of skin comprising:
    creating a volume of fluid adjacent the area of skin, said fluid having a uniformly dispersed concentration of cavitation nuclei therein; and applying ultrasound to the volume of fluid from an ultrasound transmitting element having an axis and a cross-section along said axis, said ultrasound transmitting element having a first axial end and a second axial end, said second axial end operable to produce ultrasonic waves, said first axial end comprising a matrix of ultrasound producing portions, said portions defined by a first series of parallel axial cuts and a second series of parallel axial cuts, said second series of parallel axial cuts are approximately perpendicular to said first series of parallel axial cuts and said matrix having the first cross-section, wherein the ultrasound producing portions, which are completely bounded by said cuts, each has a substantially rectangular cross-section parallel to said first cross-section;

wherein the ultrasound causes cavitation to begin at or around the cavitation nuclei.

19. The method of claim 18 wherein the cavitation nuclei comprise appropriately sized ceramic particles.

20. The method of claim 18 wherein the cavitation nuclei comprise appropriately sized polymer particles.

21. The method of claim 18 wherein the cavitation nuclei comprise appropriately sized titanium dioxide particles.

22. The method of claim 18 wherein the cavitation nuclei comprises gas bubbles.

23. The method of claim 18 further comprising delivering a substance through the area of skin.

24. The method of claim 18 further comprising extracting analyte through the area of skin.

* * * * *